United States Patent [19]

Kim et al.

[11] 4,292,431

[45] Sep. 29, 1981

[54] PROCESS FOR THE PRODUCTION OF HYDROXYMETHYLIMIDAZOLES

[75] Inventors: Choong S. Kim; Kee J. Lee; Hong S. Kim; Yung B. Chae, all of Seoul, Rep. of Korea

[73] Assignee: Korea Institute of Science and Technology, Seoul, Rep. of Korea

[21] Appl. No.: 156,806

[22] Filed: Jun. 5, 1980

[30] Foreign Application Priority Data

Mar. 31, 1980 [KR] Rep. of Korea ............... 80-1346

[51] Int. Cl.³ .......................... C07D 233/64
[52] U.S. Cl. ....................... 548/342; 548/343
[58] Field of Search ........................... 546/342

[56] References Cited

U.S. PATENT DOCUMENTS 2,946,804  7/1960  Zaugg et al. ............ 548/342
4,063,023  12/1977  Anderson et al. ........ 548/342
4,104,473  8/1978  Sawa et al. ............. 548/342

OTHER PUBLICATIONS

Jones, R., et al., *J. Am. Chem. Soc.*, 71, 2444 (1949).
Walker, J., *Formaldehyde*, 3rd Ed., Reinhold Pub. Corp., NY, 1964, p. 218.
Theilheimer, W., *Synthetic Methods of Organic Chemistry*, vol. 8, Interscience, NY, 1954, p. 21.
Mole, T., *J. Chem. Soc.*, 2132 (1960).
House, H., Modern Synthetic Reactions, W. A. Benjamin, Inc., NY, 1965, pp. 26, 27 and 34.
Morrison, R., et al., Organic Chemistry, 3rd Ed., Allyn and Bacon, Boston, 1973, p. 709.

*Primary Examiner*—Richard A. Schwartz
*Attorney, Agent, or Firm*—Holman & Stern

[57] ABSTRACT

This invention discloses a process for the production of hydroxymethylimidazoles which comprises reacting imidazolecarboxylic acids, their esters or inorganic salts with a formaldehyde agent in the presence of an alkali in an aqueous medium.

24 Claims, No Drawings

PROCESS FOR THE PRODUCTION OF HYDROXYMETHYLIMIDAZOLES

BACKGROUND OF THE INVENTION

The present invention relates to a process for the manufacture of hydroxymethylimadazoles. More particularly, this invention relates to a new and improved process for the manufacture of hydroxymethylimadazoles of formula I

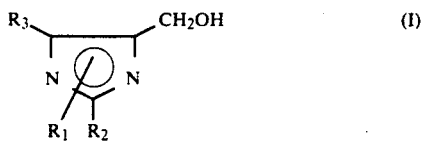

wherein $R_1$ is hydrogen, a loweralkyl, cycloalkyl, aryl or aralkyl which is located on any one of the two nitrogen atoms in the imidazole nucleus; and $R_2$ and $R_3$ are independently hydrogen, a loweralkyl, cycloalkyl, aryl and aralkyl, as well as inorganic and organic acid addition salts thereof.

As used herein the term "loweralkyl" means both a straight and branched chain $C_1$–$C_6$ alkyl (e.g., methyl, ethyl, propyl, isopropyl, n-butyl, isobutyl, t-butyl, n-pentyl, isopentyl, t-pentyl, neopentyl, n-hexyl and the like).

The term "cycloalkyl" means a cycloalkyl having a 3 to 6 membered ring(e.g., cyclopropyl, cyclopentyl, cyclohexyl and the like).

The term "aryl" means phenyl, a phenyl optionally substituted by one or more radicals selected from the group consisting of a $C_1$–$C_6$ alkyl (e.g., methyl, ethyl, propyl, isopropyl, n-butyl, isobutyl, t-butyl, n-pentyl, isopentyl, t-pentyl, neopentyl, n-hexyl and the like), halogen (e.g., chlorine, bromine, fluorine), a $C_1$–$C_6$ alkoxy (e.g., methoxy, ethoxy, propoxy, isopropoxy and the like), trifluoromethyl, nitro and cyano, or naphthyl group.

The term "aralkyl" means phen($C_1$–$C_3$)alkyl, in which the phenyl nucleus may be substituted by one or more radicals selected from the group consisting of a $C_1$–$C_6$ alkyl (e.g., methyl, ethyl, propyl, isopropyl, n-butyl, isobutyl, t-pentyl, n-pentyl, isopenyl, t-butyl, neopentyl, n-hexyl and the like), halogen (e.g., chlorine, bromine and fluorine), a $C_1$–$C_6$ alkoxy, (e.g., methoxy, ethoxy, propoxy, isopropoxy and the like), trifluoromethyl, nitro and cyano, or naphthyl group.

Certain hydroxymethylimidazoles of formula I are known compounds and are useful as starting materials for the preparation of therapeutically valuable N"-cyano-N-methyl-N'-{2-[(5-methylimidazol-4-yl)methylthio]ethyl} guanidines (See J. Med. Chem. 20,901,1977), one of which is known generically as cimetidine and has been therapeutically used in the treatment of duodenal ulcer and pathological hypersecretory conditions.

Hydroxymethylimadazoles of the types described herein have been prepared by a variety of means known to the prior art.

In one prior art process described in J. Amer. Chem. Soc. 71,2444,1949, the hydroxymethylimidazoles are prepared by reducing an imidazolecarboxylic acid ester with $LiAlH_4$ under anhydrous conditions. A similar process is described in J. Med. Chem. 20,901,1977 and British Pat. No. 1,338,169 and is hereinafter referred to as Method A.

In yet another prior art process disclosed in German OLS No. 2,637,670, the hydroxymethylimidazoles are prepared by reducing an imidazolecarboxylic acid ester with a combined use of an alkali metal and liquid ammonia under anhydrous conditions and is hereinafter referred to as Method B.

In German OLS No. 2,538,621, a process is disclosed for producing the hydroxymethylimidazoles by electrochemical reduction of an imidazolecarboxylic acid ester and is hereinafter referred to as Method C.

Another process of the prior art for the production of hydroxymethylimidazoles involves hydroxymethylation of an imidazole with formaldehyde under pressure and is hereinafter referred to as Method D. (See J. Chem. Soc. 99,2052,1911; and ibid 3128,1927).

The prior art processes described above have certain inherent disadvantages. For instance, Method (A) involves the use of an expensive and hazardous $LiAlH_4$ as a reducing agent. Additionally, the reaction must be carried out in a substantially anhydrous environment.

Method (B) again involves the use of a hazardous alkali metal. Furthermore, this process involves the use of liquid ammonia in which the reaction is conducted at extremely low temperatures, such as $-70°$ C., so that the process requires special equipment and therefore is not economically attractive for industrial application.

In commercialization of Method (C), substantial capital investment is required to obtain an expensive electrolyzer. Therefore, this method again is not economically attrative.

Method (D) suffers from several disadvantages, including a very low yield of the final products, difficulty in separation of the starting material from the final product produced and the need for application of high pressure.

It is therefore an object of the present invention to overcome these disadvantages associated with the prior art processes.

It is another object of this invention to provide a process for the production of hydroxymethylimidazoles in an aqueous medium.

It is a further object of this invention to provide a simple and economical process for the production of hydroxymethylimidazoles.

Now we have unexpectedly and surprisingly discovered a process for the manufacture of hydroxymethylimidazoles of formula I, which comprises reacting a compound of formula II

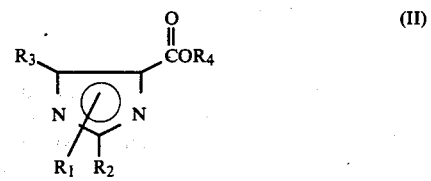

wherein $R_1$, $R_2$ and $R_3$ are as defined above and $R_4$ is hydrogen or a $C_1$–$C_6$ alkyl, with a formaldehyde agent in the presence of an alkali in an aqueous medium, or treating a compound of formula III

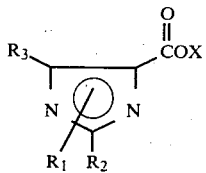

(III)

wherein $R_1$, $R_2$ and $R_3$ are as defined above and X is an alkali cation with a formaldehyde agent in an aqueous medium and, if appropriate, in the presence of an alkali.

In accordance with the process of the present invention, the compounds of formula I can be converted, if desired, to inorganic and organic acid addition salts. Suitable inorganic acids include hydrochloric acid, hydrobromic acid, sulfuric acid and the like. Suitable organic acids include picric acid, fumaric acid, maleic acid, pamoic acid, p-toluenesulfonic acid and the like.

Suitable formaldehyde agents or sources of formaldehyde for use in the process of the present invention include aqueous formaldehyde, paraformaldehyde and formaldehyde alkali metal bisulfites.

Suitable alkalies include the hydroxides, carbonates and bicarbonates of alkali metal and the hydroxides, oxides and carbonates of alkali earth metal. Representive alkalies are sodium hydroxide, potassium hydroxide, lithium hydroxide, calcium hydroxide, barium hydroxide, calcium oxide, barium oxide, sodium carbonate, potassium carbonate, sodium bicarbonate and potassium bicarbonate.

Suitable alkali cations include alkali metal and alkali earth metal cations, such as sodium, potassium, lithium, barium and calcium ions.

The process of the present invention is expediently carried out in an aqueous medium, if appropriate, admixed with a water-miscible organic solvent. Suitable organic solvents include 1,4-dioxane, tetrahydrofuran, ethyleneglycol and dimethoxyethylether. 1,4-Dioxane is preferred.

The proportion of water to the organic solvent is in the range of 1:4 by volume, preferably in the range of 1:1 by volume.

The temperature of the reaction is not critical. The reaction is operative over a wide temperature range, that is, from 30° C. to the reflux temperature of the reaction mixture. Lower temperatures can be used, but are of no advantage, since the reaction appears to proceed at lower temperatures.

The reaction of the present process is preferably carried out at a temperature from about 60° C. to the reflux of the reaction mixture and most preferably at a temperature of from about 80° C. to the reflux.

In accordance with the process of the present invention, the compounds of formula II or III are generally reacted with the formaldehyde agent in a molar ratio of from 1:1 to 1:4. A molar ratio of from 1:2.5 to 1:3 is preferred.

As previously mentioned, when the compounds of formula II are used as the reactants in the present process, the reaction is advantageously affected by the addition of alkali to the reaction system.

A stoichiometric amount or an excess of the alkali is generally required for this purpose. The molar ratio of the compounds of formula II to the alkali reactant varies depending on the type of bases employed. For instance, when an alkali metal base is employed, the molar ratio of the compounds of formula II to the alkali is from 1:1 to 1:3. A molar ratio of from 1:1.5 to 1:2 is preferred. When an alkali earth metal is used as the alkali source, the molar ratio of the compounds of formula II to the alkali is from 1:0.5 to 1:2. A molar ratio of from 1:0.7 to 1:1 is preferred.

In one embodiment of the process of the present invention, in which the compounds of formula III is reacted with the formaldehyde agent in an aqueous medium, the reaction is expediently carried out, optionally, in the presence of an alkali as hereinabove mentioned. The amount of alkali used for this purpose is from about 0.1 to about 1.0 mole per mole of the compounds of formula III.

The compounds of formula II may be prepared by methods known per se. (See. Chem. Ber. 91,988,1958). They can be obtained by condensing a 2-chloroacetoacetic acid ester with formamide.

The compounds of formula III may be prepared by simply treating the compounds of formula II with stoichiometric amounts of the bases indicated above.

The following examples further illustrate the present invention, but they are not construed to limit the scope of the invention.

EXAMPLE 1

Preparation of 4-hydroxymethyl-5-phenylimidazole

To a suspension of 2.16 g (0.01 mol) of 4-carbethoxy-5-phenylimidazole in 10 ml of water was added 0.8 g (0.02 mol) of sodium hydroxide. The mixture was heated to reflux for 2 hours. To this mixture was added 4 ml of ~37% aqueous formaldehyde solution, and the resultant mixture was heated at 60°–65° C. for 8 hours, with stirring. After completion of the reaction, the reaction mixture was cooled and the resultant solid was recovered by filtration, washed with water and recrystallized from ethyl acetate and filtered to give 1.18 g of 4-hydroxymethyl-5-phenylimidazole, m.p. 175°–176° C. Yield 68%.

Calc'd for $C_{10}H_{10}N_2O$ (Percent): C,68.96; H,5.75: N, 16.09: Found: C,68.78; H,5.83: N, 16.12: It was identified by NMR and IR as 4-hydroxymethyl-5-phenylimidazole. 4-Hydroxymethyl-5-phenylimidazole hydrochloride, m.p. 185°–186° C.

EXAMPLE 2

Preparation of 4-hydroxymethyl-5-methylimidazole hydrochloride 1.64 g (0.01 mol) of potassium 5-methylimidazole-4-carboxylate was dissolved in a mixture of 3 ml of ~37% aqueous formaldehyde and 3 ml of 1,4-dioxane. To this mixture was added 0.56 g (0.01 mol) of potassium hydroxide, and the resultant mixture were heated at 80°–90° C. for 3 hours, with stirring. After completion of the reaction, the solvent was stripped off in vacuo, and the remaining residue was extracted with absolute ethanol. To the ethanol extract was passed dry hydrogen chloride gas and concentrated to give 1.07 g of crystalline 4-hydroxymethyl-5-methylimidazole hydrochloride, m.p. 242°–244° C. Yield 72%.

It was identified by NMR and IR as 4-hydroxymethyl-5-methylimidazole hydrochloride.

EXAMPLE 3

Preparation of 4-hydroxymethylimidazole

A mixture of 4-carbethoxyimidazole (1.4 g, 0.01 mol) and potassium hydroxide (1.12 g, 0.02 mol) in water (5 ml) is heated to reflux for 30 min. To the reaction mixture is then added paraformaldehyde (2 g) and 1,4-dioxane (5 ml). The mixture is heated at 70°–80° C. for 4 hours with stirring. After completion of the reaction, the solvent is stripped off in vacuo. The residue was extracted with ethyl acetate and concentrated to give 4-hydroxymethylimidazole as a powdered solid, m.p. 88°–90° C.; picrate, m.p. 204°–206° C.

EXAMPLE 4

Preparation of 1,5-dimethyl-4-hydroxymethylimidazole

A mixture of 1,5-dimethylimidazole-4-carboxylic acid (1.4 g, 0.01 mol), potassium hydroxide (1.12 g, 0.02 mol) and ~37% aqueous formaldehyde solution (3 ml) was heated at 80°–90° C. for 3 hours. After completion of the reaction, the solvent was stripped off in vacuo, and the residue was extracted with isopropanol (40 ml). The isopropanol extract was concentrated to give a crude product. The crude solid was recrystallized from acetone and filtered to afford 0.88 g of 1,5-dimethyl-4-hydroxymethylimidazole as a white crystal, m.p. 161°–163° C. Yield 70%.

EXAMPLE 5

Preparation of 4-isopropyl-5-hydroxymethylimidazole

A mixture of 4-isopropylimidazole-5-carboxylic acid (1.54 g, 0.01 mol), calcium oxide (0.56 g, 0.01 mol) and ~37% aqueous formaldehyde solution (4 ml) is heated at 70°–80° C. for 3 hours, with stirring. After completion of the reaction, the solvent is stripped off, and the residue is extracted with acetone. The acetone extract is concentrated, and the resultant residue is recrystallized from ethyl acetate and filtered to give 4-isopropyl-5-hydroxymethylimidazole as a solid, m.p. 125°–127° C.

EXAMPLE 6

Preparation of 4-ethyl-5-hydroxymethylimidazole hydrochloride

To a solution of 1.4 g (0.01 mol) of 4-ethylimidazole-5-carboxylic acid dissolved in a mixed solvent of 10 ml of water and 5 ml of 1,4-dioxane are successively added 2.52 g (0.03 mol) of sodium bicarbonate and 2 g of paraformaldehyde. The mixture is heated at 60°–70° C. for 4 hours. After completion of the reaction, the reaction mixture is concentrated to dryness, and the residue is extracted with acetone. The acetone extract is concentrated to give a viscous oil. The viscous oil is dissolved in ethanol, and dry HCl gas is passed to yield 4-ethyl-5-hydroxymethylimidazole hydrochloride as a crystal, m.p.138°–142° C.

EXAMPLE 7

Preparation of 4-hydroxymethyl-2-phenylimidazole

To a suspension of 1.88 g (0.01 mol) of 2-phenylimidazole-4-carboxylic acid in a mixture of 3 ml of ~37% formaldehyde and 3 ml of 1,4-dioxane is added 2.1 g (0.02 mol) of sodium carbonate, and the resultant mixture is heated at 60°–70° C. for 5 hours, with stirring. After completion of the reaction, 5 ml of water is added, and the mixture is allowed to stand for 2 hours, on cooling. The resultant solid is recovered by filtration and recrystallized from ethyl acetate and filtered to afford 2-phenyl-4-hydroxymethylimidazole as a solid, m.p.168°–170° C.

EXAMPLE 8

Preparation of 1-methyl-5-hydroxymethylimidazole

To a suspension of 1.4 g (0.01 mol) of 1-methyl-5-carbmethoxyimidazole in 5 ml of water is added 0.8 g (0.02 mol) of sodium hydroxide, and the mixture was heated to reflux for 2 hours. To the mixture is added 4 ml of ~37% aqueous formaldehyde solution, and the resultant mixture is heated at 80–90 for 2 hours. After completion of the reaction, the solvent is stripped off and the residue is extracted with ethyl acetate. The ethyl acetate extract was concentrated to give 1-methyl-5-hydroxymethylimidazole as a solid, m.p. 112°–114° C.

EXAMPLE 9

Preparation of 1-isopropyl-5-hydroxymethylimidazole 1.68 g (0.01 mol) of 1-isopropyl-5-carbmethoxyimidazole is suspended in 5 ml of water. To the suspension are added 0.8 g (0.02 mol) of sodium hydroxide and 4 ml of ~37% aqueous formaldehyde. The resultant mixture is heated to reflux for 2 hours. After completion of the reaction, the solvent is stripped off, and the residue is extracted with ethyl acetate and concentrated to give 1-isopropyl-5-hydroxymethylimidazole as a solid, m.p. 83°–84° C.

EXAMPLE 10

Preparation of 1-cyclohexyl-5-hydroxymethylimidazole

To a suspension of 2.1 g (0.01 mol) of 1-cyclohexyl-5-carbmethoxyimidazole in 6 ml of water are added 0.8 g (0.02 mol) of sodium hydroxide and 4 ml of ~37% aqueous formaldehyde solution. The resultant mixture is heated at 80°–90° C. for about 2 hours. After completion of the reaction, the solvent is stripped off, and the remaining residue is extracted with ethyl acetate. The ethyl acetate extracted is concentrated to give 1-cyclohexyl-5-hydroxymethylimidazole as a solid, m.p. 133°–134° C.

EXAMPLE 11

Preparation of 1-benzyl-5-hydroxymethylimidazole

To a suspension of 2.16 g (0.01 mol) of 1-benzyl-5-carbmethoxyimidazole in 5 ml of water are succesively added 0.8 g (0.02 mol) of sodium hydroxide and 4 ml of ~37% aqueous formaldehyde. The resultant mixture is heated to reflux for 2 hours. After completion of the reaction, the solvent is stripped off, and the residual solid is extracted with ethyl acetate. The ethyl acetate extract is concentrated to give 1-benzyl-5-hydroxymethylimidazole as a solid, m.p. 138°–140° C.

EXAMPLE 12

Preparation of 1-phenyl-5-hydroxymethylimidazole

To a suspension of 2.16 g (0.01 mol) of 1-phenyl-5-carbethoxyimidazole in 5 ml of water are added 0.8 g (0.02 mol) of sodium hydroxide and then 4 ml of ~37% aqueous formaldehyde. The mixture is heated at 80°–90° C. for 2 hours. The reaction mixture is concentrated in vacuo, and then the residue is extracted with ethyl acetate. The ethyl acetate extract is concentrated to give 1-phenyl-5-hydroxymethylimidazole as a solid, m.p. 81°–84° C.

EXAMPLE 13

Preparation of 1,4-dimethyl-5-hydroxymethyl imidazole

To a suspension of 1.68 g (0.01 mol) of 1,4-dimethyl-5-carbethoxyimidazole in 10 ml of water was added 0.8 g (0.02 mol) of sodium hydroxide. The mixture was heated to reflux for 30 min. Thereafter, 3.54 g (0.03 mol) of formaldehyde sodium bisulfite was added and heated to reflux for 4 hours. The water in the reaction mixture was removed, and the residue was extracted with isopropyl alcohol and filtered. The isopropyl alcohol extract was concentrated, and the residual solid recrystallized from ethyl acetate and filtered to afford 0.46 g of 1,4-dimethyl-5-hydroxymethylimidazole as a white powdered solid, m.p. 125°–127° C.

EXAMPLE 14

Preparation of 4-hydroxymethyl-5-methylimidazole

A mixture of 1.48 g (0.01 mol) of 5-methylimidazole-4-carboxylic acid sodium salt, 2 ml of ~37% aqueous formaldehyde solution, 0.2 g (0.005 mol) of sodium hydroxide, and 3 ml of water was heated at 75°–80° C. for 3 hours. After completion of the reaction, the mixture was extracted with boiling acetone. The acetone extract was concentrated to give a solid. This solid was recrystallized from ethyl acetate to afford 0.73 g of 4-hydroxymethyl-5-methylimidazole, m.p. 136°–138° C. Yield 65%.

EXAMPLE 15

Preparation of 4-hydroxymethyl-5-methylimidazole hydrochloride

A mixture of 1.48 g (0.01 mol) of 5-methylimidazole-4-carboxylic acid sodium salt, 2 ml of ~37% formaldehyde solution and 3 ml of 1,4-dioxane was heated at 75°–85° C. for 3 hours. After completion of the reaction, the solvent was stripped off, and the remaining residue was extracted with isopropanol. The isopropanol extract was concentrated to give a viscous oil. This viscous oil was dissolved in absolute ethanol and dry hydrogen chloride gas was passed through the resulting solution to afford 0.93 g of 4-hydroxymethyl-5-methylimidazole hydrochloride, m.p. 241°–244° C. Yield 63%.

What is claimed is:

1. A process for the production of an hydroxymethylimidazole of formula I or an organic or inorganic acid addition salt thereof

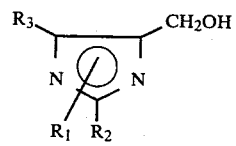 (I)

wherein $R_1$ represents hydrogen, a loweralkyl, cycloalkyl, aryl or aralkyl which is located on any one of the two nitrogen atoms in the imidazole nucleus; and $R_2$ and $R_3$ each independently represents hydrogen, a loweralkyl, cycloalkyl, aryl or aralkyl, which comprises reacting a compound of formula II

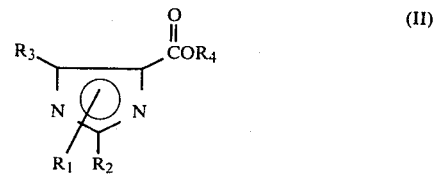 (II)

wherein $R_1$, $R_2$ and $R_3$ are as defined above and $R_4$ is hydrogen or a $C_1$–$C_6$ alkyl, with a source of formaldehyde in the presence of an alkali in an aqueous medium and optionally treating the resultant compound of Formula I with an organic or inorganic acid.

2. The process according to claim 1 wherein said source of formaldehyde is selected from the group consisting of an aqueous formaldehyde solution, paraformaldehyde and formaldehyde alkali metal bisulfites.

3. The process according to claim 1 wherein said source of formaldehyde is an aqueous formaldehyde solution.

4. The process according to claim 1 wherein the temperature of reaction is maintained between about 30° C. to the reflux temperature of the reaction mixture.

5. The process according to claim 1 wherein a molar ratio of the compounds of formula II to the source of formaldehyde is from 1:1 to 1:4.

6. The process according to claim 1 wherein a molar ratio of the compounds of formula II to the source of formaldehyde is from 1:2.5 to 1:3.

7. The process according to claim 1 wherein said alkali is selected from the group consisting of the hydroxides, carbonates and bicarbonates of alkali metals, and the hydroxides, oxides and carbonates of alkaline earth metals.

8. The process according to claim 1 wherein said alkali is selected from the group consisting of sodium hydroxide, potassium hydroxide, lithium hydroxide, calcium hydroxide, barium hydroxide, calcium oxide, barium oxide, sodium carbonate, potassium carbonate, sodium bicarbonate and potassium bicarbonate.

9. The process according to claim 1, wherein said alkali is added in an amount which is equal to or greater than a stoichiometric amount.

10. The process according to claim 1 wherein said aqueous medium is admixed with a water-miscible organic solvent.

11. The process according to claim 10, wherein said water-miscible organic solvent is selected from the group consisting of 1,4-dioxane, tetrahydrofuran, ethyleneglycol and dimethoxyethyl ether.

12. A process for the production of an hydroxymethylimidazole of formula I or an organic or inorganic acid solution salt thereof

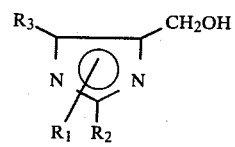 (I)

wherein $R_1$ represents hydrogen, a loweralkyl, cycloalkyl, aryl or aralkyl which is located on any one of the two nitrogen atoms in the imidazole nucleus; and $R_2$ and $R_3$ each independently represents hydrogen, a loweralkyl, cycloalkyl, aryl or aralkyl which comprises reacting a compound of formula III

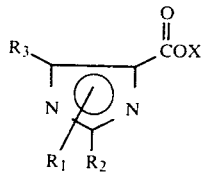

(III)

wherein $R_1$, $R_2$ and $R_3$ are as defined above and X is an alkali cation, with a source of formaldehyde in an aqueous medium and optionally treating the resultant compound of formula I with an organic or inorganic acid.

13. The process according to claim 12 wherein X is an alkali metal or alkaline earth metal cation.

14. The process according to claim 12 wherein said source of formaldehyde is selected from the group consisting of an aqueous formaldehyde solution, paraformaldehyde and formaldehyde alkali metal bisulfites.

15. The process according to claim 12 wherein said source of formaldehyde is an aqueous formaldehyde solution.

16. The process according to claim 12 wherein the temperature of reaction is maintained between about 30° C. to the reflux of the reaction mixture.

17. The process according to claim 12 wherein a molar ratio of the compounds of formula III to the source of formaldehyde is from 1:1 to 1:4.

18. The process according to claim 12 wherein a molar ratio of the compounds of formula III to the source of formaldehyde is from 1:2.5 to 1:3.

19. The process according to claim 12 wherein the reaction is effected in the presence of an alkali.

20. The process according to claim 19 wherein said alkali is selected from the group consisting of the hydroxides, carbonates and bicarbonates of alkali metals, and the hydroxides, oxides and carbonates of alkaline earth metals.

21. The process according to claim 19 wherein the amount of alkali is from about 0.1 to about 1 mole per mole of the compounds of formula III.

22. The process according to claim 12 wherein said aqueous medium is admixed with a water-miscible organic solvent.

23. The process according to claim 22 wherein said water-miscible organic solvent is selected from the group consisting of 1,4-dioxane, tetrahydrofuran, ethyleneglycol and dimethoxyethyl ether.

24. The process according to claim 1 or 12, wherein said hydroxymethylimidazole is 4-hydroxymethyl-5-methylimidazole.

* * * * *